(12) United States Patent
Kohichi et al.

(10) Patent No.: US 7,045,680 B2
(45) Date of Patent: *May 16, 2006

(54) TRANSGENIC ZOYSIAGRASS WITH REDUCED SHADE AVOIDANCE

(75) Inventors: Tohyama Kohichi, Sunchon (KR);
Jeon-Gu Kang, Kwangju (KR);
Hyo-Yeon Lee, Sunchon (KR);
Jeong-Il Kim, Kwangju (KR);
Pill-Soon Song, Kwangju (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 554 days.

This patent is subject to a terminal disclaimer.

(21) Appl. No.: 10/268,838

(22) Filed: Oct. 11, 2002

(65) Prior Publication Data

US 2004/0072353 A1    Apr. 15, 2004

(51) Int. Cl.
*C12N 15/82* (2006.01)
*C12N 15/90* (2006.01)
*A01H 5/00* (2006.01)

(52) U.S. Cl. ..................... 800/278; 435/468

(58) Field of Classification Search ............... 435/468; 800/278

See application file for complete search history.

(56) References Cited

U.S. PATENT DOCUMENTS

2003/0204872 A1* 10/2003 Kim et al. ................. 800/282

OTHER PUBLICATIONS

Taylor et al., Plant Cell Rep., 1993, vol. 12, pp. 491-495.*
Inokuma et al., Plant Cell Rep., 1998, vol. 17, pp. 334-338.*
Boylan et al., "Oat Phytochrome is Biologically Active in Transgenic Tomatoes", *The Plant Cell*, vol. 1, 765-773, Aug., 1989.
Choi et al, "Phytochrome signalling mediated through nucleoside diphosphate kinase 2," *Nature*, vol. 401, Oct. 1999.
Fankhauser et al., "PKS1, a Substrate Phosphorylated by Phytochrome That Modulates Light Signaling in Arabidopsis," *Science*, vol. 284, May 28, 1999.
Lapko et al., "Posttranslational Modification of Oat Phytochrome A: Phosphorylation Specific Serine In a Multiple Serine Cluster," *Biochemistry* 1997, vol. 36, pp. 10595-10599.
Ni et al., "PIF3, a Phytochrome-Interacting Factor Necessary for Normal Photoinduced Signal Transduction, Is a Novel Basic Helix-Loop-Helix Protein," *Cell*, vol. 95, 657-667, Nov. 25, 1999.
Park et al., "Inter-domain crosstalk in the phytochrome molecules," *Cell & Development Biology*, vol. 11, 449-456, 2000.
Smith et al., "The shade avoidance syndrome: multiple responses mediated by multiple phytochromes," *Plant, Cell and Environment*, vol. 20, pp. 840-844 (1997).
Stockhaus et al., "Serine-to-alanine substitutions at the amino-terminal region of phytochrome a result in an increase in biological activity," *Genes & Development*, vol. 6, pp. 2364-2372 (1992).
Yeh et al., "Eukaryotic phyytochromes: Light-regulated serine/threonine protin kinases with histidine kinase ancestry," *Proc. National Academy Science, USA* 13976-13981, Nov. 1988.

* cited by examiner

*Primary Examiner*—Ashwin Mehta
(74) *Attorney, Agent, or Firm*—Kenyon & Kenyon LLP

(57) ABSTRACT

The present invention provides transgenic zoysiagrass plant cells transformed with a modified oat phytochrome A gene (S598A) in which the serine-598 codon was replaced with an alanine codon, which, when expressed, significantly suppresses shade avoidance reactions, such as dwarfish internodes and petioles, short leaves, increased branching, and dark-green leaf color. Said transgenic zoysiagrass shows a robust appearance and is expected to show enhanced resistance to biotic and abiotic stresses. Also provided are a recombinant DNA construct comprising the S598A gene which, when expressed, induces drastic suppression of shade avoidance reactions, transgenic plants produced by this method, and propagating seeds obtained from said transgenic plants.

2 Claims, 4 Drawing Sheets

```
TCTGATATGTTGTTCCGAGAAGCCTCTCCCCTGACTATCGTATCAGGGACCCCCAATATC  1320
 S  D  M  L  F  R  E  A  S  P  L  T  I  V  S  G  T  P  N  I    440
ATGGACCTAGTCAAATGTGATGGTGCTGCTCTTCTGTATGGGGGAAAAGTATGGCGTCTG  1380
 M  D  L  V  K  C  D  G  A  A  L  L  Y  G  G  K  V  W  R  L    460
CGTAATGCTCCAACGGAGTCTCAGATACATGATATCGCCTTCTGGCTATCAGATGTTCAC  1440
 R  N  A  P  T  E  S  Q  I  H  D  I  A  F  W  L  S  D  V  H    480
AGGGATTCCACTGGCCTGAGTACTGACAGCCTCCATGATGCTGGCTATCCAGGAGCTGCT  1500
 R  D  S  T  G  L  S  T  D  S  L  H  D  A  G  Y  P  G  A  A    500
GCTCTTGGTGATATGATTTGTGGAATGGCAGTGGCTAAGATCAACTCCAAGGATATTCTT  1560
 A  L  G  D  M  I  C  G  M  A  V  A  K  I  N  S  K  D  I  L    520
TTTTGGTTCAGGTCACATACAGCTGCTGAAATCAGATGGGGAGGTGCAAAGAATGATCCA  1620
 F  W  F  R  S  H  T  A  A  E  I  R  W  G  G  A  K  N  D  P    540
TCGGACATGGATGACAGCAGAAGGATGCACCCTAGGTTGTCTTTCAAAGCTTTCCTTGAA  1680
 S  D  M  D  D  S  R  R  M  H  P  R  L  S  F  K  A  F  L  E    560
GTTGTCAAGATGAAGAGCTTGCCTTGGAGTGACTATGAAATGGATGCTATTCATTCATTG  1740
 V  V  K  M  K  S  L  P  W  S  D  Y  E  M  D  A  I  H  S  L    580
                                                        GCT
CAACTTATACTGCGAGGGACACTAAATGATGCCAGCAAGCCAAAGCGGGAAGCTAGTTTA  1800
 Q  L  I  L  R  G  T  L  N  D  A  S  K  P  K  R  E  A  S  L    600
                                                        A
GATAACCAGATTGGTGATCTAAAACTTGATGGGCTTGCTGAACTGCAGGCCGTGACCAGT  1860
 D  N  Q  I  G  D  L  K  L  D  G  L  A  E  L  Q  A  V  T  S    620
GAAATGGTTCGTCTAATGGAAACAGCAACTGTTCCAATCTTGGCAGTAGATGGCAATGGA  1920
 E  M  V  R  L  M  E  T  A  T  V  P  I  L  A  V  D  G  N  G    640
CTGGTCAACGGGTGGAATCAGAAAGCAGCGGAGTTGACTGGGCTAAGAGTTGATGATGCA  1980
 L  V  N  G  W  N  Q  K  A  A  E  L  T  G  L  R  V  D  D  A    660
ATTGGAAGGCACATACTTACCCTTGTGGAGGACTCCTCTGTACCAGTTGTCCAGAGGATG  2040
 I  G  R  H  I  L  T  L  V  E  D  S  S  V  P  V  V  Q  R  M    680
CTATATCTAGCTCTGCAGGGTAAAGAAGAGAAGGAAGTTCGATTTGAGGTAAAGACTCAT  2100
 L  Y  L  A  L  Q  G  K  E  E  K  E  V  R  F  E  V  K  T  H    700
GGCCCGAAGAGGGATGATGGTCCAGTTATCTTGGTTGTGAATGCTTGTGCCAGTCGGGAC  2160
 G  P  K  R  D  D  G  P  V  I  L  V  V  N  A  C  A  S  R  D    720
CTTCATGATCATGTTGTTGGAGTGTGCTTTGTTGCCCAAGATATGACTGTCCATAAGTTG  2220
 L  H  D  H  V  V  G  V  C  F  V  A  Q  D  M  T  V  H  K  L    740
```

Photosensory Domain

Hinge Region

Regulatory Domain

FIG. 1

SEQUENCE LISTING

<160> NUMBER OF SEQ ID NOS: 2

<210> SEQ ID NO 1
<211> LENGTH: 3390
<212> TYPE: DNA
<213> ORGANISM: Avena sp.

<400> SEQUENCE: 1

```
atgtcctcct caaggcctgc ttccagttct tccagcagga accgccagag ctcccaggca      60
agggtgttag cacagacaac ccttgatgcc gagctcaatg ctgaatatga agaatctggt     120
gactcctttg actactccaa gctggttgaa gcccagcggg atggtccacc tgtgcagcaa     180
gggcggtcgg agaaggtcat agcctactta cagcacattc agaaaggaaa gctaatccaa     240
acatttggtt gcctgttggc ccttgatgag aagagcttca atgtcatcgc gttcagtgag     300
aacgcgccag aaatgcttac aacggtcagc catgcggtac ccagtgttga tgatccccca     360
aggctgggga ttggcaccaa tgtacggtct cttttcagtg accaaggtgc cacagcactg     420
cataaggcac taggatttgc tgatgtgtct ttgctgaatc ctatcctggt tcagtgcaag     480
acatcaggca agcctttcta tgccattgtt catcgagcaa ctggttgttt ggtggtagac     540
tttgagcctg taaagcctac agaatttcct gccactgctg ctggggcttt gcagtcctac     600
aagcttgctg ccaaggcaat atccaagatc cagtcattgc caggtggaag catggaggtg     660
ctatgcaata ctgtggtgaa ggaagtcttt gaccttaccg ggtatgacag ggttatggct     720
tacaagtttc atgaagatga ccatggtgag gtattctccg aaatcacaaa gcctggtctt     780
gagccttatc taggcctgca ctatccagcc actgacatcc ctcaagcagc caggtttctt     840
ttcatgaaga acaaagtacg gatgatttgt gattgccgtg cgagatccat aaaggtcatt     900
gaagctgagg cactccccct tgatattagc ctatgtggtt cagcactcag ggcaccacac     960
agttgtcacc ttcagtatat ggagaacatg aactcgattg catcccttgt catggctgtt    1020
gtggttaatg agaatgaaga ggatgatgaa gctgagtctg aacaaccagc acagcagcag    1080
aaaaagaaga actatgggg cctccttgtt tgccaccatg agagcccag atatgtccct    1140
tttccgctgc gttatgcttg tgagttctta gcacaggtgt ttgctgtcca tgtcaacagg    1200
gagtttgaat tagagaaaca gttgcgtgag aagaacatac tgaagatgca aacaatgctc    1260
tctgatatgt tgttccgaga agcctctccc ctgactatcg tatcagggac ccccaatatc    1320
```

```
atggacctag tcaaatgtga tggtgctgct cttctgtatg ggggaaaagt atggcgtctg    1380
cgtaatgctc caacggagtc tcagatacat gatatcgcct tctggctatc agatgttcac    1440
agggattcca ctggcctgag tactgacagc ctccatgatg ctggctatcc aggagctgct    1500
gctcttggtg atatgatttg tggaatggca gtggctaaga tcaactccaa ggatattctt    1560
ttttggttca ggtcacatac agctgctgaa atcagatggg gaggtgcaaa gaatgatcca    1620
tcggacatgg atgacagcag aaggatgcac cctaggttgt ctttcaaagc tttccttgaa    1680
gttgtcaaga tgaagagctt gccttggagt gactatgaaa tggatgctat tcattcattg    1740
caacttatac tgcgagggac actaaatgat gccagcaagc caaagcggga agctgctcta    1800
gataaccaga ttggtgatct aaaacttgat gggcttgctg aactgcaggc cgtgaccagt    1860
gaaatggttc gtctaatgga aacagcaact gttccaatct ggcagtaga tggcaatgga    1920 ctggtcaacg ggtggaatca gaaagcagcg gagttgactg gctaagagt tgatgatgca    1980 attggaaggc acatacttac ccttgtggag gactcctctg taccagttgt ccagaggatg    2040
ctatatctag ctctgcaggg taaagaagag aaggaagttc gatttgaggt aaagactcat    2100
ggcccgaaga gggatgatgg tccagttatc ttggttgtga atgcttgtgc cagtcgggac    2160
cttcatgatc atgttgttgg agtgtgcttt gttgcccaag atatgactgt ccataagttg    2220
gtgatggaca gtttactcg ggttgagggt gactacaagg cgatcattca aacccgaac    2280 ccactcattc ctcctatatt tggtgctgac gaatttggat ggtgttcgga gtggaatgct    2340
gcaatgacca agttgactgg gtggaataga gatgaagtgc tcgataagat gcttcttggt    2400
gaagtgtttg acagtagcaa tgcttcctgc cctttgaaga acagagatgc atttgtaagt    2460
ctttgtgttc ttatcaacag tgcattagcc ggggaagaaa cagaaaaggc tccatttggc    2520
ttcttcgaca gaagtggaaa gtacattgag tgtcttctat cagcaaacag aaaagaaaat    2580
gagggtggtc tcatcactgg agtattctgt tttattcatg ttgctagtca tgagctgcaa    2640
catgcactac aggtgcagca agcctcggag caaacgtcgc taaaaaggct caaggctttc    2700
tcctacatga gacatgcgat caacaaccct ctctcaggca tgctctactc tagaaaagca    2760
ttgaagaaca cagatttgaa tgaagaacag atgaagcaga ttcatgttgg agataattgt    2820
caccaccaga taaacaagat acttgcagac ttggatcaag atagcatcac cgaaaaatct    2880
agctgcttgg atttggagat ggctgaattt ctgttgcaag atgtggtggt ggctgctgta    2940
agtcaagtac tgataacctg ccagggaaaa gggatcagaa tctcttgcaa cctgccagag    3000
agatttatga agcagtcagt ctatggagat ggtgttcgac tccagcagat cctctctgac    3060
ttcctgttta tttcagtgaa gttctctcct gttggaggtt ctgttgagat tcttccaag    3120 ctgacaaaga acagcatcgg agaaaacctt catcttattg accttgaact taggatcaag    3180
caccagggat taggagtccc agcagagctc atggcacaaa tgtttgagga ggacaacaag    3240
gagcagtcag aggagggctt gagcctccta gtttctagaa acctgctgag gctcatgaat    3300
ggtgatgttc ggcatctaag ggaagctggt gtgtcaacct tcatcatcac cgctgaactt    3360
gcttccgctc aacagcaat gggacaatga                                      3390
```

<210> SEQ ID NO 2
<211> LENGTH: 1129
<212> TYPE: PRT
<213> ORGANISM: Avena sp.

<400> SEQUENCE: 2

```
Met Ser Ser Ser Arg Pro Ala Ser Ser Ser Ser Arg Asn Arg Gln
1               5                   10                  15

Ser Ser Gln Ala Arg Val Leu Ala Gln Thr Thr Leu Asp Ala Glu Leu
            20                  25                  30

Asn Ala Glu Tyr Glu Ser Gly Asp Ser Phe Asp Tyr Ser Lys Leu
            35                  40                  45

Val Glu Ala Gln Arg Asp Gly Pro Pro Val Gln Gln Gly Arg Ser Glu
50                  55                  60

Lys Val Ile Ala Tyr Leu Gln His Ile Gln Lys Gly Lys Leu Ile Gln
65                  70                  75                  80

Thr Phe Gly Cys Leu Leu Ala Leu Asp Glu Lys Ser Phe Asn Val Ile
                85                  90                  95

Ala Phe Ser Glu Asn Ala Pro Glu Met Leu Thr Thr Val Ser His Ala
            100                 105                 110

Val Pro Ser Val Asp Asp Pro Arg Leu Gly Ile Gly Thr Asn Val
            115                 120                 125

Arg Ser Leu Phe Ser Asp Gln Gly Ala Thr Ala Leu His Lys Ala Leu
            130                 135                 140

Gly Phe Ala Asp Val Ser Leu Leu Asn Pro Ile Leu Val Gln Cys Lys
145                 150                 155                 160

Thr Ser Gly Lys Pro Phe Tyr Ala Ile Val His Arg Ala Thr Gly Cys
                165                 170                 175

Leu Val Val Asp Phe Glu Pro Val Lys Pro Thr Glu Phe Pro Ala Thr
            180                 185                 190

Ala Ala Gly Ala Leu Gln Ser Tyr Lys Leu Ala Ala Lys Ala Ile Ser
            195                 200                 205

Lys Ile Gln Ser Leu Pro Gly Gly Ser Met Glu Val Leu Cys Asn Thr
210                 215                 220

Val Val Lys Glu Val Phe Asp Leu Thr Gly Tyr Asp Arg Val Met Ala
225                 230                 235                 240

Tyr Lys Phe His Glu Asp Asp His Gly Glu Val Phe Ser Glu Ile Thr
                245                 250                 255

Lys Pro Gly Leu Glu Pro Tyr Leu Gly Leu His Tyr Pro Ala Thr Asp
            260                 265                 270

Ile Pro Gln Ala Ala Arg Phe Leu Phe Met Lys Asn Lys Val Arg Met
            275                 280                 285

Ile Cys Asp Cys Arg Ala Arg Ser Ile Lys Val Ile Glu Ala Glu Ala
        290                 295                 300

Leu Pro Phe Asp Ile Ser Leu Cys Gly Ser Ala Leu Arg Ala Pro His
305                 310                 315                 320

Ser Cys His Leu Gln Tyr Met Glu Asn Met Asn Ser Ile Ala Ser Leu
            325                 330                 335

Val Met Ala Val Val Val Asn Glu Asn Glu Glu Asp Asp Glu Ala Glu
            340                 345                 350

Ser Glu Gln Pro Ala Gln Gln Lys Lys Lys Leu Trp Gly Leu
            355                 360                 365

Leu Val Cys His His Glu Ser Pro Arg Tyr Val Pro Phe Pro Leu Arg
        370                 375                 380

Tyr Ala Cys Glu Phe Leu Ala Gln Val Phe Ala Val His Val Asn Arg
385                 390                 395                 400

Glu Phe Glu Leu Glu Lys Gln Leu Arg Glu Lys Asn Ile Leu Lys Met
                405                 410                 415

Gln Thr Met Leu Ser Asp Met Leu Phe Arg Glu Ala Ser Pro Leu Thr
```

-continued

```
                420             425             430
Ile Val Ser Gly Thr Pro Asn Ile Met Asp Leu Val Lys Cys Asp Gly
            435                 440                 445
Ala Ala Leu Leu Tyr Gly Gly Lys Val Trp Arg Leu Arg Asn Ala Pro
            450                 455                 460
Thr Glu Ser Gln Ile His Asp Ile Ala Phe Trp Leu Ser Asp Val His
465                 470                 475                 480
Arg Asp Ser Thr Gly Leu Ser Thr Asp Ser Leu His Asp Ala Gly Tyr
                485                 490                 495
Pro Gly Ala Ala Ala Leu Gly Asp Met Ile Cys Gly Met Ala Val Ala
            500                 505                 510
Lys Ile Asn Ser Lys Asp Ile Leu Phe Trp Phe Arg Ser His Thr Ala
            515                 520                 525
Ala Glu Ile Arg Trp Gly Gly Ala Lys Asn Asp Pro Ser Asp Met Asp
            530                 535                 540
Asp Ser Arg Arg Met His Pro Arg Leu Ser Phe Lys Ala Phe Leu Glu
545                 550                 555                 560
Val Val Lys Met Lys Ser Leu Pro Trp Ser Asp Tyr Glu Met Asp Ala
                565                 570                 575
Ile His Ser Leu Gln Leu Ile Leu Arg Gly Thr Leu Asn Asp Ala Ser
            580                 585                 590
Lys Pro Lys Arg Glu Ala Ala Leu Asp Asn Gln Ile Gly Asp Leu Lys
            595                 600                 605
Leu Asp Gly Leu Ala Glu Leu Gln Ala Val Thr Ser Glu Met Val Arg
            610                 615                 620
Leu Met Glu Thr Ala Thr Val Pro Ile Leu Ala Val Asp Gly Asn Gly
625                 630                 635                 640
Leu Val Asn Gly Trp Asn Gln Lys Ala Ala Glu Leu Thr Gly Leu Arg
                645                 650                 655
Val Asp Asp Ala Ile Gly Arg His Ile Leu Thr Leu Val Glu Asp Ser
                660                 665                 670
Ser Val Pro Val Val Gln Arg Met Leu Tyr Leu Ala Leu Gln Gly Lys
            675                 680                 685
Glu Glu Lys Glu Val Arg Phe Glu Val Lys Thr His Gly Pro Lys Arg
            690                 695                 700
Asp Asp Gly Pro Val Ile Leu Val Val Asn Ala Cys Ala Ser Arg Asp
705                 710                 715                 720
Leu His Asp His Val Val Gly Val Cys Phe Val Ala Gln Asp Met Thr
                725                 730                 735
Val His Lys Leu Val Met Asp Lys Phe Thr Arg Val Glu Gly Asp Tyr
                740                 745                 750
Lys Ala Ile Ile His Asn Pro Asn Pro Leu Ile Pro Pro Ile Phe Gly
            755                 760                 765
Ala Asp Glu Phe Gly Trp Cys Ser Glu Trp Asn Ala Ala Met Thr Lys
            770                 775                 780
Leu Thr Gly Trp Asn Arg Asp Glu Val Leu Asp Lys Met Leu Leu Gly
785                 790                 795                 800
Glu Val Phe Asp Ser Ser Asn Ala Ser Cys Pro Leu Lys Asn Arg Asp
                805                 810                 815
Ala Phe Val Ser Leu Cys Val Leu Ile Asn Ser Ala Leu Ala Gly Glu
            820                 825                 830
Glu Thr Glu Lys Ala Pro Phe Gly Phe Phe Asp Arg Ser Gly Lys Tyr
            835                 840                 845
```

-continued

```
Ile Glu Cys Leu Leu Ser Ala Asn Arg Lys Glu Asn Glu Gly Gly Leu
    850             855                 860

Ile Thr Gly Val Phe Cys Phe Ile His Val Ala Ser His Glu Leu Gln
865                 870                 875                 880

His Ala Leu Gln Val Gln Gln Ala Ser Glu Gln Thr Ser Leu Lys Arg
                885                 890                 895

Leu Lys Ala Phe Ser Tyr Met Arg His Ala Ile Asn Asn Pro Leu Ser
                900                 905                 910

Gly Met Leu Tyr Ser Arg Lys Ala Leu Lys Asn Thr Asp Leu Asn Glu
            915                 920                 925

Glu Gln Met Lys Gln Ile His Val Gly Asp Asn Cys His His Gln Ile
    930                 935                 940

Asn Lys Ile Leu Ala Asp Leu Asp Gln Asp Ser Ile Thr Glu Lys Ser
945                 950                 955                 960

Ser Cys Leu Asp Leu Glu Met Ala Glu Phe Leu Leu Gln Asp Val Val
                965                 970                 975

Val Ala Ala Val Ser Gln Val Leu Ile Thr Cys Gln Gly Lys Gly Ile
            980                 985                 990

Arg Ile Ser Cys Asn Leu Pro Glu Arg Phe Met Lys Gln Ser Val Tyr
        995             1000                1005

Gly Asp Gly Val Arg Leu Gln Ile Leu Ser Asp Phe Leu Phe
    1010            1015                1020

Ile Ser Val Lys Phe Ser Pro Val Gly Gly Ser Val Glu Ile Ser
    1025            1030                1035

Ser Lys Leu Thr Lys Asn Ser Ile Gly Glu Asn Leu His Leu Ile
    1040            1045                1050

Asp Leu Glu Leu Arg Ile Lys His Gln Gly Leu Gly Val Pro Ala
    1055            1060                1065

Glu Leu Met Ala Gln Met Phe Glu Glu Asp Asn Lys Glu Gln Ser
    1070            1075                1080

Glu Glu Gly Leu Ser Leu Leu Val Ser Arg Asn Leu Leu Arg Leu
    1085            1090                1095

Met Asn Gly Asp Val Arg His Leu Arg Glu Ala Gly Val Ser Thr
    1100            1105                1110

Phe Ile Ile Thr Ala Glu Leu Ala Ser Ala Pro Thr Ala Met Gly
    1115            1120                1125

Gln
```

TRANSGENIC ZOYSIAGRASS WITH REDUCED SHADE AVOIDANCE

SEQUENCE LISTING

The instant application contains a Sequence Listing which has been submitted via CD-R, and is hereby incorporated by reference in its entirety. Said CD-Rs, created on Sep. 16, 2005, are labeled "Copy 1 Replacement", "Copy 2 Replacement" and "CRF Replacement", respectively, each contains one identical 40 KB file identified as 1942.52 Sequence Listing.txt.

FIELD OF THE INVENTION

The present invention relates to a field of manipulation of growth rate and light responsiveness of crop plants via genetic transformation with a modified phytochrome A photoreceptor. It is particularly concerned with a modification of plant architecture and photomorphogenesis by molecular biological strategies to engineer responses to environmental light of economically important crop plants, with an emphasis on turfgrass, particularly transgenic turfgrass with apparent dwarfish and more branched architecture. The invention is accomplished by developing transgenic crop plants through suppression of shade avoidance reactions. As a result, the transgenic plants are healthy and robust and more resistant to pathogen infections. In addition, they can cover the ground and recover from traffic damages more quickly than parental plants, thereby providing plants of high economic value with improved adaptive plasticity.

BACKGROUND OF THE INVENTION

The present invention relates to transgenic zoysiagrass (*Zoysia japonica* Steud.) comprising plant cells transformed with a recombinant DNA construct containing a nucleotide sequence which encodes a modified oat phytochrome A, in which serine-598 was substituted with alanine to improve light responsiveness. The resultant transgenic zoysiagrass exhibits significant reduction of typical shade avoidance reactions, such as dwarfish internodes and petioles, short leaves, dark-green leaf color, and healthy and robust appearance, which greatly affects yields and environmental adaptation of crop plants.

Zoysiagrass, which is also known as Korean grass, is one of the most widely cultivated turfgrass species in the temperate zone worldwide, especially in the Far-Eastern Asia, including Korea, Japan, and Eastern area of China. The cultivation area is rapidly expanding in recent years in USA and other countries due to its unusual characteristics such as drought resistance and rapid recovering capacity from traffic damages. Particularly, it grows well even in poor soil under virtually all climates. It is therefore widely used for both practical and decoration purposes, such as in golf courses, athletic fields, roadsides, home gardens, and riverbanks. However, zoysiagrass has some intrinsic drawbacks whose resolution is strongly demanded by the customers. Major concerns include improved resistance to pathogens and herbicides and adaptive plasticity to environmental changes. In addition, zoysiagrass tends to overgrow during the hot summer season and require frequent watering and mowing that is labor-consuming and costly. Of particular concern is that the overgrown plant is very susceptible to fungal infections, and vast amount of chemicals, including fungicides, should be spread to control various pathogens, which resultantly causes a serious environmental pollution. One efficient way to solve these problems in zoysiagrass cultivation is to genetically engineer it so that it exhibits reduced shade avoidance responses. Shade avoidance is an adaptive mechanism for plants to overcome severe light competition occurring in nature (Smith and Whitelam, 1997). When plants grow in the dark or shade, which is naturally represented under the canopy of neighboring plants, stem or hypocotyl extension is drastically stimulated at the expense of leaf and root growth, resulting in elongated but weak and pale appearance. As a result, they are very susceptible to pathogen infections and environmental stress, causing significant loss of crop productivities. Genetically engineered zoysiagrass with reduced shade avoidance reactions will grow slower but healthier than parental plants. With well-established plant molecular biological and plant tissue culture techniques available to plant biologists, it is now possible to introduce any particular gene of interest into virtually any crop plant and to introduce or improve useful traits in a predictable way.

Plant growth and development is regulated through coordinate interactions between intrinsic developmental cues, such as growth hormones, and various environmental factors. Light is one of the most important environmental factors that influences many aspects of plant growth and developmental processes throughout the whole life span, covering from seed germination, leaf and stem growth, photoperiodism, shade avoidance, to flowering, which are collectively called photomorphogenesis. One prominent photomorphogenic response critical for survival and propagation for plants in nature is the shade avoidance. It is a well-known plant vegetation dynamic process that is absolutely required to overcome severe light competition occurring in nature, especially when plants grow in close proximity, as naturally occurring in forests and frequently encountered in densely cultivated area. Shade avoidance response is typified by abnormally fast extension growth of stems and petioles but with suppressed leaf and root growth and storage organ production to get sufficient light required for photosynthesis, resulting in elongated but weak and pale appearance. Although it is an essential mechanism for plant survival, it could be a potential problem in crop cultivation, since crop plants become slender, weak, and pale and susceptible to pathogen infections and environmental changes, such as rain and wind. There have been diverse efforts to resolve this problem in crop cultivation, and it has been recently found that manipulation of shade avoidance reactions is a promising way to achieve this.

The proximity signal that induces shade avoidance reactions in plants is the radiation reflected from neighboring plants. Photosynthetic pigments absorb most of the visible light wavelengths (400–700 nm), but lights with longer wavelengths (700–800 nm) in the far-red light range is reflected or transmitted, resulting in prevalence of far-red (FR) light wavelength under canopy. FR light is perceived by the phytochrome photoreceptors. The physiological function of the phytochromes is primarily driven by a unique photochemical activity, reversible phototransformation between two distinct spectral forms, the red (R) light absorbing Pr form and the FR light absorbing Pfr form. The Pfr form is responsible for physiological functions in most photomorphogenic processes. It is therefore evident that the phytochrome action is determined by the R:FR ratio in the light environment. There are at least five different phytochromes (phyA to phyE) known in Arabidopsis. They exert both overlapping as well as distinct functions. In etiolated plants, phyA are accumulated to a high level and inhibits stem growth in response to light, with the λmax being around 710–720 nm. However, in light-grown plants, phyA is rapidly degraded, and phyB has a primary role in modulation of stem growth as a function of R:FR ratio. When FR content is high, as occurred under canopy, phyB modulates the shade avoidance reactions. As a consequence, FR light inhibits stem growth mainly via phyA action in etiolated plants but stimulates stem growth in light-grown plants primarily via phyB action.

It has been clearly established that in transgenic plants overexpressing phyA, the phyA level is maintained to a certain level sufficient to offset light-induced degradation and exhibits a severe dwarfism when grown in light environment that contains relatively high content of FR wavelength. Although engineering of shade avoidance by introducing a foreign PHYA gene was successful in dicotyledonous plants (Boylan and Quail, 1989), transgenic rice plants that overexpress a PHYA gene did not show such a dwarfish appearance. Two possibilities have been suggested to explain the absence of dwarfish appearance in transgenic rice plants. First, monocotyledonous or dicotyledonous phytochrome may have a distinct function, each specifically functioning in each plant group. Alternatively, the expression level of the phyA was not enough to offset the light-induced degradation of the intrinsic phyA, possibly due to inefficient action of the promoter employed. Since all phyAs isolated from both monocotyledonous and dicotyledonous plants show high sequence homologies and exhibit identical photochemical activities, we assumed that the latter might be the reason for the absence of any phenotypic alterations in the transgenic rice plants expressing a foreign phyA.

We recently obtained an oat phyA mutant, in which serine-598 was substituted with alanine, that showed a hypersensitive light response. Transgenic model plants expressing the modified phyA were more severely dwarfish than those expressing a wild type phyA when grown in the light. Based on this observation, it was anticipated that transgenic turfgrass or rice with the modified phyA would cause reduced shade avoidance reactions, more prominently than that with the wild type phyA, irrespective of the presence or absence of neighboring plants.

As used herein, the term "genetic transformation" refers to a procedure to introduce a gene(s) or genetic material(s) into a crop plant of interest in a predictable way. The gene or genetic material is stably integrated into the plant genome and transmitted through generations as a part of the plant genome.

SUMMARY OF THE INVENTION

The present invention, entitled "Transgenic Zoysiagrass" with Reduced Shade Avoidance, relates to a genetic transformation of zoysiagrass with a modified oat phytochrome A gene (SEQ ID NO: 1) to engineer light responsiveness in various aspects of photomorphogenic growth and development, among which reduced shade avoidance responses, such as dwarfish appearance and increased branching, is the most prominent. Similar genetic approaches can be applied for the genetic transformations of closely related turfgrass species or other monocot plants, such as rice.

The oat phytochrome A gene (PHYA) used in the present invention is a modified version (S598A) of the wild type gene in which serine-598 is substituted with alanine. The codon for serine, AGT, was changed to GCT, a codon for alanine, by site-directed in vitro mutagenesis. As a whole, the phytochrome molecule consists of two major structural domains, the N-terminal photosensory domain with a covalently bound chromophore, phytochromobilin, at cysteine-321 residue (Bhoo et al, 1999), and the C-terminal regulatory domain that contains several structural motifs required for phytochrome dimerization and protein kinase (Yeh and Lagarias, 1998). It also contains structural elements that directly interact with diverse phytochrome interacting factors, such as PIF3 (Ni et al, 1998), PKS1 (Fankhauser et al, 1999), and NDPK2 (Choi et al, 1999). Serine-598 is located in the small hinge region between the two structural domains. Particularly, it is the only serine residue that is autophosphorylated selectively in the Pfr form in vivo. It has been therefore suggested that serine-598 mediates the phytochrome function by modulating the inter-domain signaling within the phytochrome molecule (Lapko et al, 1997). We recently observed that Arabidopsis plants transformed with the modified PHYA gene (S598A) exhibited a hypersensitive light response, serious reaction of shade avoidance reactions, further supporting a critical role for serine-598 in the phytochrome function.

The present invention provides a transgenic zoysiagrass that overexpresses the S598A gene under the control of a constitutive ubiquitin promoter (Ubi-P). Transgenic line was isolated by herbicide resistance.

The calli of transgenic zoysiagrass are internationally deposited under Budapest Treaty under deposit No. KCTC 10242BP with international depositary authority on May 10, 2002, that is, Korean Collection for Type Cultures address of which is Korean Research Institute of Bioscience and Biotechnology #52, Oun-dong, Yusong-ku, Taejon 305–333, Republic of Korea.

The resultant transgenic zoysiagrass exhibits strong suppression of the typical shade avoidance responses. The observed phenotypic changes included dwarfish internodes and petioles, short leaves, more branching, and dark-green leaf color, which are agronomically useful traits in crop plants. Since the transgenic zoysiagrass is dwarfish but healthy (dark-green and robust), it would show improved recovering capacity from traffic damages and resistance to pathogens. In addition, less frequent mowings and waterings would be required.

These results with transgenic zoysiagrass expressing the S598A gene indicate that transgenic crop plants with reduced shade avoidance reactions can be generated through similar molecular approach. They will be able to grow healthier but at higher density, an agronomical trait that is useful specifically in rice and other monocot plants. Furthermore, the transgenic plants will need less nutrients and water and chemicals for growth and pathogen control, respectively.

Therefore, the present invention provides: 1. a method for generation of transgenic zoysiagrass (*Zoysia japonica* Steud.) or close related turfgrass species with a modified oat phytochrome A gene (SEQ ID NO: 1) (S598A). 2. a transgenic zoysiagrass with the S598A gene that exhibits dwarfish internodes and petioles, short leaves, more branching, and dark-green leaf color (deposited as KCTC 10242BP).

BRIEF DESCRIPTION OF THE DRAWINGS

FIG. 1 shows a nucleotide sequence (SEQ ID NO: 3) portion of the oat phytochrome A gene (GenBank Accession Number 16110) and the corresponding amino acid sequence (SEQ ID NO: 4) containing the serine-598. The phyA consists of two functional domains, the N-terminal photosensory and the C-terminal regulatory domains, that are connected by a hinge region. The serine-598 (S) is located in the hinge region and substituted with alanine (A) by site-directed in vitro mutagenesis as indicated.

DETAILED DESCRIPTION OF THE INVENTION

Figure 2:
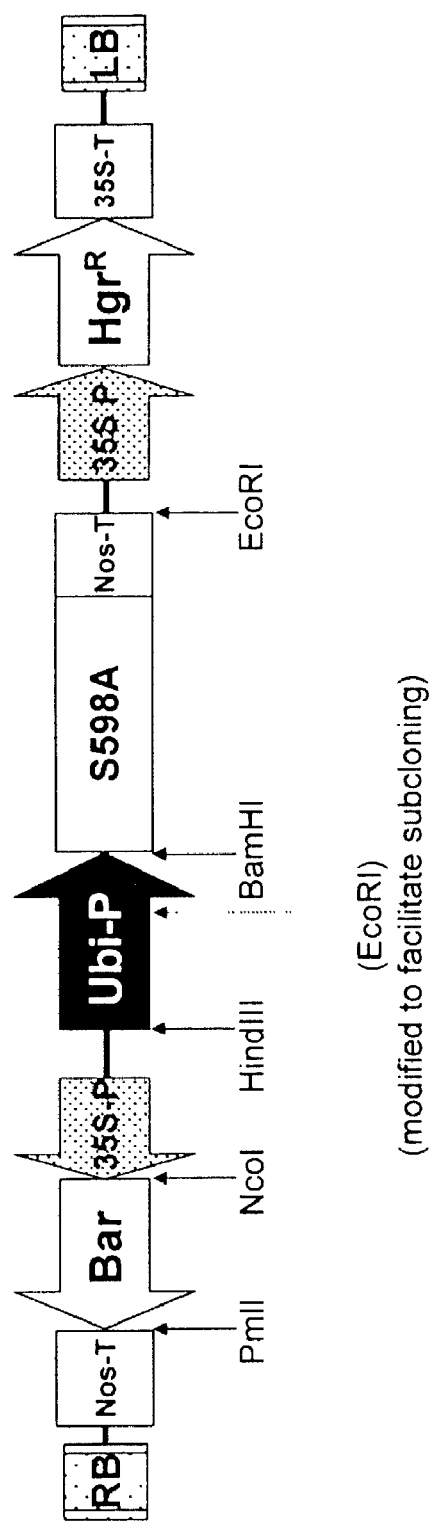
FIG. 2 shows a recombinant plant expression vector construct with the modified phytochrome A gene (S598A). The S598A gene transcription is driven by a constitutive ubiquitin promoter (Ubi-P). The plant expression vector contains a kanamycin resistance gene (Kan$^R$) for bacterial selections in E. coli and Agrobacterium tumefaciens) and a herbicide resistance gene (Bar) and a hygromycin resistance gene (Hgr$^R$) for selections in plants. The Bar and Hgr$^R$ expressions are driven by a CaMV 35S promoter (35S-P). The S598A gene was ligated using the unique BamHI and EcoRI sites. An EcoRI site originally present within the Ubi-P promoter was modified so that subsequent subclonings are facilitated. RB and LB: right and left borders, respectively. Nos-T and 35S-T: NOS and 35S terminator sequences, respectively.
Figure 3:
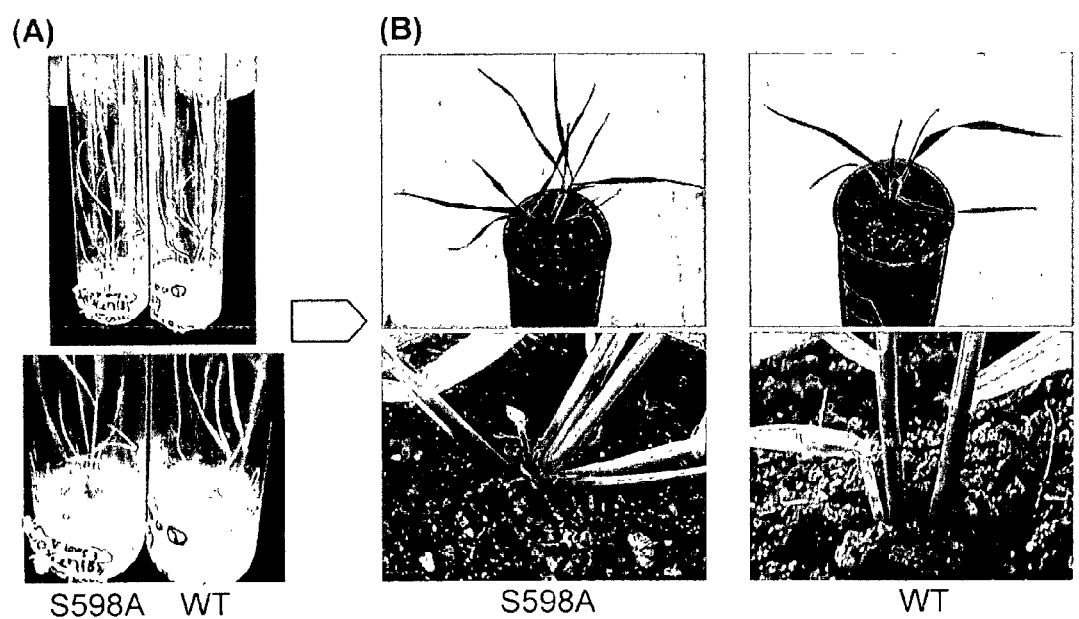
FIG. 3 shows a transgenic zoysiagrass seedling grown on MS medium containing 5 mg/liter bialaphos (A). Transgenic (S598A) and control (WT) seedlings were grown under the same experimental conditions. The plants were transferred to soil and further grown (B). Note that the phenotypic changes, such as short leaves (upper panel) and more branching (lower panel), are more evident.
Figure 4:
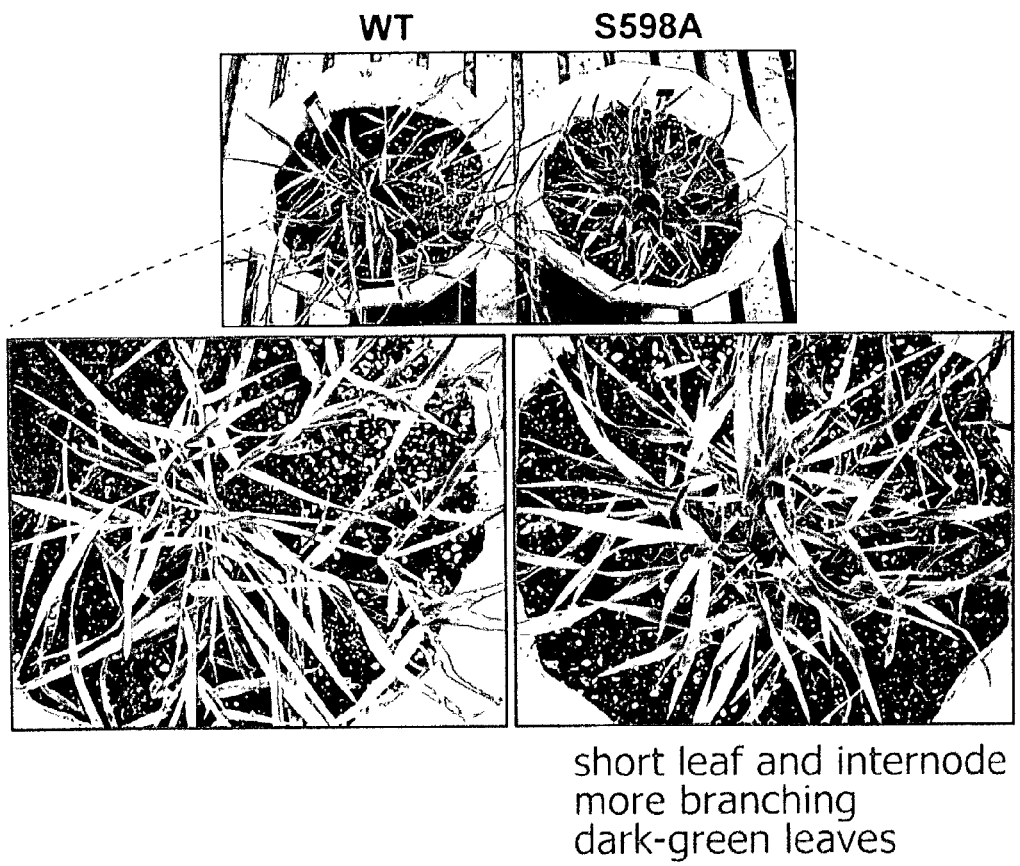
FIG. 4 shows an adult transgenic zoysiagrass grown in soil. The transgenic zoysiagrass plant (S598A) with the modified phytochrome A gene (S598A) exhibits dwarfish internodes and petioles, short leaves, and more branching compared to control plants. Note that the leaves of the transgenic zoysiagrass plant have dark-green color, possibly due to chloroplast condensation within the plant cells.

Genetic transformation of crop plants with a gene or gene segment of interest is a recently established way to efficiently develop new varieties of plant species with novel or enhanced useful traits. Potential target traits suitable for genetic manipulation of crop plants include modified growth rate, adaptive plasticity, enhanced resistance to biotic and abiotic stress, and improved yield. With recently advanced techniques and knowledge in plant molecular biology and tissue culture, any gene of interest can be routinely introduced into any particular plant species. An efficient system for genetic transformation and tissue culture has been developed for zoysiagrass, and high-level expression of introduced genes has been confirmed in the transgenic zoysiagrass (Bae et al, 2001).

The detailed description of the present invention is disclosed to assist those skilled in the art in practicing the present invention. However, modifications and alterations of the present invention may be possible by the ordinary skilled in the art unless it does not diverge from the direction and scope of the present invention.

The present invention provides transgenic monocotyledonous or dicotyledonous plants that exhibit reduced shade avoidance reactions, such as dwarfish stems (hypocotyls) and petioles, short leaves, more branching, and dark-green color, particularly transgenic zoysiagrass and related turfgrass species and rice plants comprising plant cells transformed with a recombinant DNA construct containing a gene sequence encoding a modified oat phytochrome A (SEQ ID NO: 2), that is functionally linked to at least one expression regulatory sequence element required for proper expression of said gene in plants, causing maintenance of the said gene expression to a high level and conferring on said plant the capacity to suppress shade avoidance reactions.

Definitions

"Maintenance of the expression" means;

(1) that although the intrinsic phytochrome A is light-labile and rapidly degraded upon light illumination, additional phytochrome A is continuously supplied from the transgene to a level that is sufficient to offset or even surpass the loss by light-stimulated degradation by the gain; or (2) that the normal biological activity of the phytochrome A is modified in a way that its physiological activity is greatly improved compared to that of the wild type phytochrome A.

Said modified phytochrome A is generated by substituting serine-598 or its functional equivalent (s) in oat phytochrome A or other phytochrome As, respectively, from dicotyledonous or monocotyledonous plants. Said modified phytochrome A (SEQ ID NO: 2) can possess similar or even greater physiological activity compared to that of wild type phytochrome A in suppressing shade avoidance reactions.

Said modified phytochrome A gene (S598A) may be applied through conventional genetic transformation procedures, applied using the examples provided in the present invention, and by other methods well known to the skilled in the art.

"Reduced shade avoidance reactions" refer to the suppression of shade avoidance responses; the stimulation of extension growth of stems (hypocotyls) and petioles at the cost of leaf and root growth modulated by the proximity signal (R: FR ratio) perceived by the phytochrome photoreceptors, such that stems (or internodes) and petioles become dwarfish, branching is increased, and leaf color becomes dark-green due to chloroplast condensation in plant cells. The reduction of shade avoidance reactions is most prominent when plants are grown in close proximity to neighboring plants.

Reduction of shade avoidance response which is useful in redistributing metabolites more into harvestable organs and in enhancing crop yields can be achieved either by increasing the phytochrome A expression or by modifying the normal biological activity of the phytochrome A such that its biological activity is greatly improved compared to that of the wild type one when expressed in the transgenic plants of the present invention.

For example, serine-598 is located in the hinge region between the N-terminal photosensory and the C-terminal regulatory domains and has been suggested to have a role in the inter-domain signaling from photoperception in the N-terminal domain to regulation of phytochrome interactions with PIFs in the C-terminal domain (Park et al, 2000). It is preferentially phosphorylated in the FR absorbing Pfr phytochrome and important for the phytochrome function. Substitution of serine-598 with alanine has been confirmed to cause hypersensitive light response to environmental light when expressed in model plant cells, although it exhibits identical photochemical activity to the wild type phytochrome A (Stockhaus et al, 1992).

"Expression regulatory sequence elements" refer to nucleotide sequence elements that, when properly linked to a gene or gene segment in the expression vector construct, induce efficient expression of the gene of interest to a high level and include but not limited to promoters, enhancers, repressors, and poly(A) terminator sequences. The poly(A) terminator sequence is linked to the 3' end of the desired gene and regulates the transcriptional termination at the proper site and addition of poly(A) tail which is necessary for mRNA stability and efficient translation.

For example, a promoter, which may alternatively be referred to as a gene promoter, is linked to the 5' end of the desired gene and regulates the transcriptional initiation. The promoter useful in the present invention has at least one of the following properties;
(1) constitutive expression of the desired gene or gene segment throughout the plant life span in all plant organs; or
(2) conditional expression of the desired gene or gene segment only if a specific environmental or developmental signal induces the promoter activity; or
(3) organ-specific expression of the desired gene or gene segment in specific plant organs, such as flowers, leaves, or stems; or
(4) developmental stage-specific expression of the desired gene or gene segment during a specific developmental stage, for example, in the vegetative or reproductive growth stage. Two representative promoters used in gene expression in plant cells are the cauliflower mosaic virus 35S (CaMV 35S) promoter and the maize polyubiquitin (Ubi-P) promoter. The latter is particularly useful when expressing a desired gene or gene segment in monocot plants since it is at least ten times stronger than the former.

"A plant expression vector" is defined as a recombinant DNA construct comprising at least one desired gene which is properly linked to said expression regulatory sequence elements, such as promoters and poly(A) signal sequence and results in the expression of the product of said gene to a high level.

The plant expression vector construct (pCUMB-phyA) of the present invention possesses the following characteristics.
(1) an ubiquitin promoter (Ubi-P) and a NOS terminator for the efficient expression of the desired gene; and
(2) a herbicide resistance gene (BAR) and a hygromycin resistant gene ($Hgr^R$) for selection in higher plant cells; and
(3) a kanamycin resistance gene ($Kan^R$) for bacterial selections in *E. coli* and *A. tumefaciens*; and
(4) a modified oat phytochrome A gene (S598A) in which serine-598 was substituted with alanine, which is inserted into the pCUMB vector by replacing the GUS-coding sequence using BamHI and EcoRI recognition sites under the control of the Ubi-P promoter.

The desired gene can be prepared either synthetically or isolated naturally. Alternatively, it can consist of a mixture of synthetic and naturally isolated DNA constituents, which encode proteins, enzymes, carrier, pumps or phytohormones. In general, synthetic DNA sequences are produced with appropriate codons, which are preferentially used for gene expression in plant cells.

"Plant transformation" refers to a procedure to introduce a gene or a cDNA of interest with appropriately linked expression regulatory sequence elements into any the art. The plants can be genetically engineered to exhibit reduced shade avoidance response by introducing the gene or cDNA in a functionally operable manner and expressing at a level effective in causing reduced shade avoidance response, thereby modifying plant architecture and growth rate.

In the present invention, zoysiagrass was used as a host plant for the expression of said modified oat phytochrome A gene (S598A). Such transgenic zoysiagrass displays dwarfish internodes and petioles, short leaves, and increased branching. It will also show an enhanced capacity to flexibly adapt to environmental changes and improved resistance to pathogen infections. Additionally, regular maintenance cost required for mowing and watering will be greatly decreased in the cultivation of such transgenic zoysiagrass.

EXAMPLES

Plant Expression Vector Construction

A cDNA encoding the oat phytochrome A3 gene (GenBank Accession Number 16110) was isolated by reverse transcriptase-mediated polymerase chain reaction (RT-PCR) run using specific PCR primers and PfuTurbo DNA polymerase (Stratagene, La Jolla, Calif.) that possesses the 3' to 5' proofreading activity. The 5' and 3' PCR primers have a BamHI site and a EcoRI recognition sequence, respectively, to facilitate subsequent DNA manipulations. The PCR product containing the gene was double-digested with BamHI and EcoRI and ligated into the pGEM3Z(+) cloning vector that was double-digested with BamHI and EcoRI in a similar manner as with the PCR product. The QuickChange™ kit (Stratagene) was used for site-directed in vitro mutagenesis according the procedure supplied by the manufacturer. The original AGT codon of the oat phytochrome A3 gene was mutated to GCT to substitute serine-598 with alanine. The base substitutions were verified by direct DNA sequencing. The mutated phytochrome A3 gene (S598A) was subsequently subcloned into the BamHI/EcoRI-digested pCUMB vector, resulting in pCUMB-phyA vector. The pCUMB vector is a binary vector that contains resistance genes for kanamycin for bacterial selections in *E. coli* and *A. tumefaciens* and for hygromycin and herbicide for selections in plant cells. The expression of the S598A gene was under the control of a ubiquitin promoter (Ubi-P). All the intermediate and final vector constructions were verified by restriction mappings and direct DNA sequencings.

Preparation of Zoysiagrass Calli

Mature seeds of zoysiagrass (*Zoysia japonica* Steud.) were surface-sterilized with 1 ml of 2% sodium hypochlorite for 15 min and then thoroughly washed with sterilized double-distilled water three times. For callus induction, seeds were plated on 3MM filter paper-laid MS (Murashige and Skoog, 1962) medium petridish containing 3% sucrose (w/v), 100 mg/liter α-ketoglutaric acid, 4 mg/liter thiamine-HCl, 2 mg/liter 2,4-D, 0.2 mg/liter BA, and 0.2% gelrite (w/v). The medium was adjusted to pH5.8 using HCl before autoclaving at 1.2–1.3 kg/cm$^2$ pressure and 121° C. for 20 min. Callus induction was conducted in a culture room set at 26±1° C. in complete darkness for three months. After subsequent three-day incubation under continuous white light with an intensity of 30 μmol m$^{-2}$s$^{-1}$ provided by fluorescent tubes, only green tissues were transferred to a fresh MS media containing 1 mg/liter 2,4-D and 0.2 mg/liter BA and cultured in the dark for further growth. After 5 weeks of culture in the dark, independent seed-derived calli with green color were transferred and further cultured on 3 MM filter paper-laid MS media containing 2,4-D and BA in the dark. Among the four types of calli observed (types I to IV), only type III calli were further amplified on the MS media containing 4 mg/liter 2,4-D after subculturings at four-week intervals and used as host plant cells for genetic transformation.

Optimized Conditions for *Agrobacterium* Infection

An *A. tumefaciens* strain EHA105 containing the pCUMB-phyA was used for the infection of zoysiagrass calli. The *A. tumefaciens* cells were grown at 28° C. overnight with shaking at 160 rpm in 100 ml Erlenmeyer flask containing 20 ml LB medium supplemented with 50 mg/liter hygromycin and 100 mg/liter kanamycin. Cells in 10 ml of the suspension culture were collected in a 50 ml polypropylene tube (Becton Dickinson Labware, USA) by centrifugation at 2500 rpm for 20 min and resuspended in 10 ml of liquid infection medium (calcium-free MS salts and vitamins, 30 g/l sucrose, 10 g/l glucose, 100 mg/l betaine, 50 mg/l acetosyringone, 0.01% pluronic F68, 0.01 mg/l BA, and 2 g/l gelrite, pH5.2) by gentle vortexing.

Acetosyringone was prepared by dissolving an appropriate amount of powder in dimethyl sulfoxide at a final concentration of 100 mg/ml, filter-sterilized, and stored at 4° C. in the dark until use. It was directly added to the sterile medium to an appropriate final concentration whenever required. The proliferated calli were immersed in the Agrobacterial cell suspension for 1 min. After brief dehydration on sterile 3 MM filter paper, the calli were cultivated on a co-cultivation media plate, equivalent to infection medium but supplemented with 4 mg/liter 2,4-D, at 26±1° C. in the dark for 15 days. After co-cultivation, the calli were thoroughly washed by gentle vortexing in sterile double-distilled water supplemented with a surfactant (0.02% pluronic F68) until the washing solution becomes transparent and finally washed in sterile double-distilled water containing 1000 mg/liter calbenicillin and 0.02% surfactant.

The optimized conditions for efficient *A. tumefaciens* infection of zoysiagrass calli were the use of type III calli as recipient cells, a co-cultivation period of 9 days, the exclusion of 2,4-D and $CaCl_2$ from the infection media, and the use of 100 mg/l acetosyringone.

Co-cultivated calli were then transferred to 3 MM filter paper-laid MSCGCB media (MS salts and vitamins, 30 g/l sucrose, 1 mg/l 2,4-D, 0.01 mg/l BA, 2 g/l gelrite, and 500 mg/l calbenicillin, pH5.8) and cultured for 2–4 weeks in the dark. The calli were then transferred to 3 MM filter paper-laid MSSI medium (MS salts and vitamins, 30 g/l maltose, 1 mg/l BA, 2 g/l gelrite, 250 mg/l carbenicillin, pH5.8) for shoot induction. Induced shoots were subsequently transferred to MSRS medium (MS salts and vitamins, 30 g/l sucrose, 1 mg/l $GA_3$, 2 g/l gelrite, 250 mg/l carbenicillin, and 5 mg/l bialaphos or 10 mg/l hygromycin, pH5.8) for rooting and selection for 4 weeks. The rooting plants were transferred to MSPG medium (MS salts and vitamins, 30 g/l sucrose, 8 g/l agar, pH5.8) without antibiotics and bialaphos and further grown. The fully grown plants were then transferred to a pot containing soil and grown in an environmentally controlled growth chamber set at 30° C., 80% relative humidity, and 18-hour photoperiod with 30 $\mu molm^{-2}s^{-1}$ irradiance provided by cool white fluorescent tubes. When the roots developed enough, pots were transferred to green house.

Selection of Transgenic Zoysiagrass Plants

After transgenic plants were established in soil, they were sprayed with 5 g/liter herbiace solution (Meiji Seika, Japan) every day for 2 weeks. After 2 weeks of herbicide applications, transgenic plants survived from bialaphos painting and grew to maturity. However the control plants stopped growing and eventually died.

Analysis of Shade Avoidance Response of Transgenic Zoysiagrass Plants

Transgenic zoysiagrass plant with the S598A phytochrome A gene was further examined molecular biologically to confirm that it was truly transformed with the S598A gene and grown in soil in parallel to the control plants under the identical growth condition. Morphological and photomorphogenic traits that were analysed and compared included those related with shade avoidance reactions, including plant architecture, growth rates of stems and leaves, branching pattern, and color of leaves.

RESULTS

A homozygotic line of zoysiagrass (*Zoysia japonica* Steud.) transformed with a modified oat phytochrome A gene (S598A), in which serine-598 codon, AGT, was substituted with alanine codon, GCT, driven by an ubiquitin promoter was isolated, and plant architecture, growth rate, and morphology were analysed.

Serine-598 residue is located in the hinge region between the two functional domains of the phytochrome molecule and preferentially phosphorylated in the Pfr phytochrome in vivo. It was therefore suggested that it exerts a critical role in the inter-domain signaling by transducing the light signals perceived by the N-terminal photosensory domain to the C-terminal regulatory domain. Transgenic Arabidopsis plants with the modified phytochrome A gene exhibited hypersensitive light responses to environmental light, confirming the importance of the serine-598 residue in the phytochrome function. The sequence region of the oat phytochrome A containing the serine-598 and its substitution with alanine is illustrated in FIG. 1.

The S598A gene was subcloned into a plant expression vector, pCUMB, and the resultant recombinant vector construct (FIG. 2) was transformed into zoysiagrass using the recently establishes Agrobacterium-mediated method.

The transgenic zoysiagrass transformed with the S598A gene exhibited a dwarfish appearance as a whole. More specifically, internodes and petioles were significantly shortened compared to those of the wild type plants, and branching was also increased at least 2 times. In addition, the leaves had dark-green color. These phenotypic alterations are typical of transgenic model plants with enhanced the expression of phytochrome A as a result of drastic reduction of shade avoidance responses. Although the growth of the transgenic zoysiagrass plant was greatly suppressed, it is healthy and robust and expected to be more resistant to biotic and abiotic stresses, including drought, traffic damages, and pathogen infections. Furthermore, regular maintenance cost can be drastically saved since less mowing and watering are required. Of particular concern is the improved resistance to pathogen infections, especially fungal infections that are prevalent during the hot summer season. As a result, less chemical sprays are required.

It is therefore fully expected that, as is the case of the zoysiagrass employed in the present invention herein, that transgenic crop plants with the modified phytochrome A gene exhibit reduced shade avoidance reactions that will be stably and reproducibly transmitted to their progeny through generations.

The present invention as described can be obviously varied in many ways. However, such variations are not to be regarded as a departure from the limit and scope of the present invention but all such variations as being evident to the skilled in the art are intended to be included within the limit and scope of the claims listed in the invention.

REFERENCES

Bae C-H, Tohyama K, Lee S C, Lim Y P, Kim H I, Song P-S, Lee H Y (2001) Efficient plant regeneration using mature seed-derived callus in Zoysiagrass (*Zoysia japonica* Steud.). Korean J Plant Tissue Cult 28: 61–67

Bhoo S H, Hirano T, Jeong H Y, Lee J G, Furuya M, Song P-S (1997) Phytochrome photochromism probed by site-directed mutations and chromophore esterification. J. Am. Chem. Soc. 119: 11717–11718

Boylan M T, Quail P H (1989) Oat phytochrome is biologically active in transgenic tomatoes. Plant Cell 1: 765–773

Choi G, Yi H, Lee J, Kwon Y K, Soh M S, Shin B, Luka Z, Hahn T R, Song P S (1999) Phytochrome signalling is mediated through nucleoside diphosphate kinase 2. Nature 401: 610–613

Fankhauser C, Yeh K C, Lagarias J C, Zhang H, Elich T D, Chory J (1999) PKS1, a substrate phosphorylated by phytochrome that modulates light signalling in *Arabidopsis*. Science 284: 1539–1541

Lapko V N, Jiang X Y, Smith D L, Song P-S (1997) Posttranslational modification of oat phytochrome A: Phosphorylation of a specific serine in a multiple serine cluster. Biochemistry 36:10595–10599

Ni M, Tepperman J M, Quail P H (1998) PIF3, a phytochrome-interacting factor necessary for normal photoinduced signal transduction, is a novel basic helix-loop-helix protein. Cell 95: 657–667

Park C M, Bhoo S-H, Song P-S (2000) Inter-domain crosstalk in the phytochrome molecules. Cell Dev. Biol. 11: 449–456

Smith H, Whitelam G C (1997) The shade avoidance syndrome: multiple responses mediated by multiple phytochromes. Plant Cell & Environ. 20: 840–844

Stockhaus J, Nagatani A, Halfter U, Kay S, Furuya M, Chua N-H (1992) Serine to alanine substitutions at the amino-terminal region of phytochrome A results in an increase in biological activity. Genes Dev. 6: 2364–2372

Yeh K C, Lagarias J C (1998) Eukaryotic phytochromes: light-regulated serine/threonine protein kinases with histidine kinase ancestry. Proc. Natl. Acad. Sci. USA 95: 13976–13981.

What is claimed is:

1. A method for producing a genetically transformed Zoysiagrass having the property of suppression of shade avoidance, comprising the steps of:
   i. transforming cells of zoysiagrass with a recombinant DNA construct said construct comprising a corn plant ubiquitin promoter; a modified phytochrome A gene set forth in SEQ ID NO: 1; and a 3' nontranslated sequence comprising a polyadenylation signal sequence functioning in plant cells, which are operatively linked in sequence in the 5' to 3' direction;
   ii. selecting plant cells transformed with said construct;
   iii. regenerating zoysiagrass plants from cells that have been transformed with said construct; and
   iv. selecting transgenic zoysiagrass that expresses the amino acid seciuence of SEQ ID NO: 2, encoded by SEQ ID NO: 1.

2. A genetically transformed Zoysiagrass produced by the method according to claim 1, that has the property of suppression of shade avoidance.

* * * * *

UNITED STATES PATENT AND TRADEMARK OFFICE
CERTIFICATE OF CORRECTION

PATENT NO.         : 7,045,680 B2
APPLICATION NO. : 10/268838
DATED              : May 16, 2006
INVENTOR(S)        : Kohichi et al.

Page 1 of 1

It is certified that error appears in the above-identified patent and that said Letters Patent is hereby corrected as shown below:

| Column | Line | |
|---|---|---|
| 9 | 48 | Change "30 $\mu molm^{-2}s^{-1}$" to -- 30 $\mu mol^{-2}s^{-1}$ --; |
| 9 | 55 | Change "herbiace" to --Herbiace® --; |
| 10 | 30 | Change "recently establishes" to -- recently established --; and |
| 20 | 55 | Change "seciuence" to -- sequence --. |

Signed and Sealed this

Twenty-eighth Day of November, 2006

JON W. DUDAS
*Director of the United States Patent and Trademark Office*